United States Patent [19]

Ogoshi

[11] Patent Number: 4,758,553

[45] Date of Patent: Jul. 19, 1988

[54] COMPOSITIONS OF NUCLETIC ACID COMPONENTS FOR NUTRITIONAL REPLENISHMENT

[75] Inventor: Shohei Ogoshi, Kochi, Japan

[73] Assignees: Otsuka Pharmaceutical Factory, Inc., Naruto; Ajinomoto Co., Inc., Tokyo, both of Japan

[21] Appl. No.: 104,550

[22] Filed: Sep. 30, 1987

Related U.S. Application Data

[63] Continuation of Ser. No. 680,111, Dec. 10, 1984, abandoned.

[30] Foreign Application Priority Data

Dec. 9, 1983 [JP] Japan ............................ 58-233142

[51] Int. Cl.$^4$ .......................................... A61K 31/70
[52] U.S. Cl. ....................................... 514/47; 514/48; 536/27; 536/28
[58] Field of Search ...................... 514/47, 48; 536/27, 536/28

[56] References Cited

U.S. PATENT DOCUMENTS

| 2,786,051 | 3/1957 | György et al. | 536/22 |
| 3,231,385 | 1/1966 | Ziro et al. | 536/28 |
| 3,686,392 | 8/1972 | Hamada et al. | 514/47 |

OTHER PUBLICATIONS

Brevet Special de Medicament, No. 2, 441M, Apr. 6, 1964.
Au Brevet Special de Medicament, No. 54, CAM, Sep. 14, 1964.
Brevet D'Invention, No. 1,553,966, Jun. 17, 1968.
Canadian Journal of Biochemistry, vol. 54: 500–506, 1976.
Journal of Parenteral and Enteral Nutrition, vol. 106: 435–442, 1976.
ibid., vol. 109: 1377–1382, 1979.
ibid., vol. 110: 1793–1804, 1980.
ibid., vol. 106: 428–434, 1976.
Journal of Billogical Chemistry, vol. 239: 1564–1568, 1964.
Rote Liste, 1971, p. 699, Editio Cantor, Aulendorf-/Wurtt., DE; p. 699, "Laevadosin", Laevadosin-2, Laevadosin-Tabletten-buccal.
Rote Liste, 1963, p. 597, Editio Cantor, Aulendorf-/Wurtt., DE; p. 597, "Laevadoshin-Suppositorien".
Rote Liste, 1977/78, Editio Cantor, Aulendorf/Wurtt., DE; Abstract No. 56, 112 Cb, "Hepa-Diaphal Injektionslosung"; Abstract No. 67 207 B, Vitasic.
Unlisted Drugs, vol. 24, No. 11, Nov. 1972, p. 174, Chatham, NJ, US; point p, "Nucleosincroma".
Unlisted Drugs, vol. 26, No. 1, Jan. 1974, p. 11, Chatham, NJ, US; point 1, "Upase".
Unlisted Drugs, vol. 19, No. 11, Nov. 1967, p. 150, Chatham, NJ, US; point b, "Gi-Erre".
Unlisted Drugs, vol. 25, No. 1, Jan. 1973, p. 9, Chatham, NJ, US; point a, "Guaninoderm".

*Primary Examiner*—Nicky Chan
*Attorney, Agent, or Firm*—Armstrong, Nikaido, Marmelstein & Kubovcik

[57] ABSTRACT

This invention provides a composition of nucleic acid components for nutritional replenishment characterized in that the composition comprises as effective components at least two nucleic acid compounds selected from the group consisting of (a) nucleic acid bases and pharmaceutically acceptable salts thereof, (b) nucleosides and pharmaceutically acceptable salts thereof and (c) nucleotides and pharmaceutically acceptable salts thereof.

11 Claims, No Drawings

COMPOSITIONS OF NUCLETIC ACID COMPONENTS FOR NUTRITIONAL REPLENISHMENT

This application is a continuation of application Ser. No. 680,111 filed Dec. 10, 1984, now abandoned.

The present invention relates to novel compositions of nucleic acid components.

Proteins are essential components of living body and directly provide for the unique functions and activities of the living body. This has been made apparent by enzymes, hormones, antibodies, etc.

On the other hand, amino acids are the essential components of proteins, and the nucleotide sequence of DNA or RNA is said to be the eventual determinant of the amino acid arrangement of proteins. Thus, nucleic acids closely relate to the synthesis of amino acids and therefore to the synthesis of proteins. The living body is in a state of dynamic equilibrium wherein proteins are repeatedly synthesized and decomposed, and life is sustained by the conjugated presence of nucleic acids and proteins.

Typical organs which synthesize proteins are, for example, the liver which synthesizes the serum proteins, the pancreas which secretes digestive enzymes, the bone marrow which prepares blood corpuscles, muscles, etc. For the living body to maintain its nitrogen balance, the living body needs to be exogeneously supplied with proteins or amino acids which are the components thereof. Accordingly, in the case where protein metabolism is impaired, i.e., when it is impossible or difficult for the patient to orally take a diet or nutrients, for example, owing to liver diseases, gastrointestinal diseases, cancer, burn, surgery or some other causes, the patient is usually parenterally replenished with amino acids and other nutrients for the control of nutrition and the maintenance of nitrogen balance.

For this purpose, various protein preparations and amino acid preparations have been developed and made commercially available as nutrient supplements. In recent years, however, various cases have been reported wherein administration of such known protein or amino acid preparations is still unable to assure satisfactory nutrition control and maintenance of nitrogen balance. It is therefore desired to provide novel nutrient supplements.

Accordingly an object of the present invention is to provide a composition of nucleic acid components as a nutrient supplement of a novel type.

Another object of the invention is to provide a novel composition of nucleic acid components for nutritional replenishment which enhances the efficient use of the amino acids in the living body and assures satisfactory nutrition control and nitrogen balance.

Another object of the invention is to provide a novel composition of nucleic acid components for nutritional replenishment which, when given in combination with an amino acid preparation, enhances the efficient use of the amino acids present in the living body and the amino acids given and assures satisfactory nutrition control and maintenance of nitrogen balance.

Another object of the invention is to provide a method of nutritional replenishment with use of a composition of nucleic acid components which, when given to patients with impaired metabolism of proteins, enhances the efficiency of use of the amino acids present in the living body and assures satisfactory nutrition control and maintenance of nitrogen balance.

Another object of the invention is to provide a method of nutritional replenishment with use of a composition of nucleic acid components which, when given conjointly with an amino acid preparation to patients with impaired protein metabolism, enhances the efficiency of use of the amino acids present in the living body and the amino acids administered and assures satisfactory nutrition control and maintenance of nitrogen balance.

Other objects of the invention will become apparent from the following description.

The above objects of the present invention can be fulfilled by a composition of nucleic acid components for nutritional replenishment comprising as effective components at least two nucleic acid compounds selected from the group consisting of (a) nucleic acid bases and pharmaceutically acceptable salts thereof, (b) nucleosides and pharmaceutically acceptable salts thereof and (c) nucelotides and pharmaceutically acceptable salts thereof, and also by a method of nutritional replenishment whereby the composition is administered to a patient with impaired protein metabolism.

My research has revealed that when the present composition comprising at least two of nucleic acid bases, nucleosides and nucleotides which are components of nucleic acids is administered to the living body, the composition not only achieves a nutritional effect by itself but also enhances the efficiency of use of the amino acids in the living body and assures satisfactory nutrition control and maintenance of nitrogen balance. I have further found that when given in combination with a known amino acid preparation, the present composition enhances the efficiency of use of the amino acids present in the living body and the amino acids administered, and assures more satisfactory nutrition control and maintenance of nitrogen balance. It remains to be clarified how the present composition enhances the efficiency of use of the amino acids present in the living body and/or the amino acids administered and how it assures satisfactory nutrition control and maintenance of nitrogen balance. The cause of these achievements is presumed to be attributable to the followings: the nucleic acid compounds serving as the effective components of the present composition form nucleic acids in the living body to produce a nutritional effect by themselves and also to promote in vivo synthesis of proteins from the amino acids present in the living body and/or the amino acids given.

The term "nutritional replenishment" as herein used in connection with the present composition of nucleic acid components and the present method means that the composition produces a nutritional effect by itself and also that the composition enhances the efficiency of use of amino acids present in the living body and/or the amino acids given to produce a nutritional effect.

Examples of nucleic acid bases suitable as nucleic acid compounds for use in this invention are bases, such as adenine, hypoxanthine, guanine, cytosine, uracil, thymine and orotic acid, and pharmaceutically acceptable salts thereof. Of these, preferable are adenine, hypoxanthine, guanine, cytosine, uracil and thymine. Examples of suitable nucleosides are ribonucleosides such as adenosine, inosine, guanosine, cytidine, uridine and orotidine; and deoxyribonucleosides such as deoxyadenosine, deoxycytidine, deoxyguanosine, deoxyuridine and thymidine, and pharmaceutically acceptable salts of these nucleosides. Of these, preferable are adenosine, inosine, guanosine, cytidine, uridine and thymidine.

Examples of suitable nucleotides composed of such nucleosides as above and one to three phosphoric acids attached thereto are ribonucleotides such as adenosine-n'-monophosphate (AMP), adenosine-n'-diphosphate (ADP), adenosine-n'-triphosphate (ATP), inosine-n'-monophosphate (IMP), inosine-n'-diphosphate (IDP), inosine-n'-triphosphate (ITP), guanosine-n'-monophosphate (GMP), guanosine-n'-diphosphate (GDP), guanosine-n'-triphosphate (GTP), cytidine-n'-monophosphate (CMP), cytidine-n'-diphosphate (CDP), cytidine-n'-triphosphate (CTP), uridine-n'-monophosphate (UMP), uridine-n'-diphosphate (UDP) and uridine-n'-triphosphate (UTP) wherein n' is 2', 3' or 5'; and deoxyribonucleotides such as deoxyadenosine-m'-monophosphate (dAMP), deoxyadenosine-m'-diphosphate (dADP), deoxyadenosine-m'-triphosphate (dATP), deoxyguanosine-m'-monophosphate (dGMP), deoxyguanosine-m'-diphosphate (dGDP), deoxyguanosine-m'-triphosphate (dGTP), deoxycytidine-m'-monophosphate (dCMP), deoxycytidine-m'-diphosphate (dCDP), deoxycytidine-m'-triphosphate (dCTP), thymidine-m'-monophosphate (TMP), thymidine-m'-diphosphate (TDP), and thymidine-m'-triphosphate (TTP) wherein m' is 3' or 5'; and pharmaceutically acceptable salts of these nucleotides. Of these, preferable are AMP, IMP, GMP, CMP, UMP and TMP.

The nucleic acid compounds will hereinafter be represented by symbols according to the provisions of IUPAC-IUB or by symbols usually used in the art.

The composition of nucleic acid components of the present invention may comprise only two of the compounds exemplified above, but it is preferable to use at least three, more preferably four to six, of such compounds in suitable combinations.

When at least two nucleic acid components are used, preferred combinations are as follows. Although the combinations are shown in a free form, they may be similarly usable when in the form of a pharmaceutically acceptable salt.

Examples of representative combinations of two compounds are cytosine/IMP, inosine/AMP, inosine/GMP, CMP/UMP, AMP/CMP, guanosine/GMP, uridine/IMP, thymidine/dAMP, CDP/TTP, IMP/GMP, CMP/IMP, etc. Examples of representative combinations of three compounds are uracil/CMP/TMP, adenosine/inosine/IMP, inosine/AMP/UMP, AMP/CMP/GMP, UMP/TMP/IMP, cytosine/uridine/GMP, adenine/UMP/GMP, guanosine/uridine/TMP, uracil/IMP/CMP, deoxycytidine/GMP/IMP, thymidine/uracil/IMP, GMP/UMP/dCMP, etc. Examples of representative combinations of four compounds are inosine/thymidine/CMP/UMP, cytosine/thymidine/UMP/IMP, deoxyinosine/thymidine/UMP/IMP, AMP/CMP/GMP/UMP, CTP/GMP/UTP/IMP, adenine/cytosine/AMP/uridine, adenine/thymine/IMP/UMP, thymidine/GMP/UMP/IMP, thymidine/CMP/UMP/IMP, cytosine/CMP/UMP/IMP, uridine/GMP/UMP/IDP, thymine/inosine/AMP/dGMP, etc. In the case of five compounds, representative combinations are, for example, inosine/cytidine/GMP/uridine/thymidine, uridine/thymidine/CMP/GMP/IMP, inosine/thymidine/CMP/GMP/UMP, cytosine/thymidine/GMP/UMP/IMP, thymine/inosine/AMP/CMP/GMP, AMP/CMP/GMP/UMP/TMP, AMP/CTP/dGMP/UTP/IMP, cytosine/uridine/AMP/CMP/UMP, adenine/cytosine/inosine/UMP/TDP, thymine/CMP/dATP/dGMP/UTP, thymidine/AMP/CMP/GMP/UMP, thymidine/CMP/GMP/UMP/IMP, cytosine/thymidine/GMP/UMP/IMP, etc. Representative combinations of six compounds are, for example, inosine/cytidine/thymidine/CMP/GMP/UMP, cytosine/inosine/AMP/UMP/GMP/IMP, adenine/inosine/thymidineCMP/UMP/IMP, dAMP/ATP/GMP/UDP/IMP/dCMP, guanosine/inosine/uridine/UMP/IMP/dGMP, AMP/CMP/dGMP/UTP/TMP/IMP, thymidine/CMP/GMP/UMP/IMP/TMP, cytosine/thymidine/UMP/CMP/dAMP/dGMP, ATP/dCMP/GMP/UDP/TTP/IMP, etc. Representative combinations of seven compounds are, for example, inosine/uridine/thymidine/AMP/CMP/GMP/UMP, etc. Preferred combinations of eight compounds are inosine/cytidine/uridine/thymidine/CMP/GMP/IMP/UMP, etc.

The present compositions are not limited to these examples but include combinations of nine or more compounds. In the combinations exemplified above, the nucleic acid base and salt thereof, nucleoside and salt thereof with sugar attached to the above nucleic acid base and nucleotide and salt thereof with 1 to 3 phosphoric acids attached to the above nucleoside can be replaced with each other, and the replacement can achieve the same degree of intended pharmacological effect. For example, a combination of inosine/GMP/cytidine/uridine/thymidine can be replaced with inosine/GMP/cytosine/uridine/thymine, IMP/GMP/CMP/UMP/thymidine, etc.

Preferred Examples of the present compositions are those comprising four to six nucleic acid compounds selected from the group consisting of (a) nucleic acid bases selected from adenine, hypoxanthine, guanine, cytosine, uracil and thymine, and pharmaceutically acceptable salts thereof, (b) nucleosides selected from adenosine, inosine, guanosine, cytidine, uridine and thymidine, and pharmaceutically acceptable salts thereof and (c) nucleotides selected from adenosine-n'-monophosphate (AMP), inosine-n'-monophosphate (IMP), guanosine-n'-monophosphate (GMP), cytidine-n'-monophosphate (CMP), uridine-n'-monophosphate (UMP) and thymidine-n'-monophosphate (TMP), and pharmaceutically acceptable salts thereof. Of these combinations, especially preferable are those comprising four to six of nucleic acid compounds selected from nucleosides selected from adenosine, inosine, guanosine, cytidine, uridine and thymidine, and pharmaceutically acceptable salts thereof, and nucleotides selected from AMP, IMP, GMP, CMP, UMP and TMP, and pharmaceutically acceptable salts thereof. Examples of the above especially preferable combinations are CMP/UMP/IMP/thymidine, AMP/GMP/CMP/UMP/thymidine, IMP/GMP/CMP/UMP/thymidine and inosine/cytidine/GMP/uridine/thymidine. The ratio of the nucleic acid compounds to be used in combination, for example, the mole ratio thereof can be suitably determined as selected from a wide range, according to the kinds of the compounds, condition or symptoms of the patient, etc. Examples of preferable mole ratios for the above especially preferred combinations are CMP:UMP:IMP:thymidine=4:3:8:1 or 7.5:4:12.5:1, AMP:GMP:CMP:UMP:- thymidine=4:4:4:3:1, IMP:GMP:CMP:UMP:thymidine=4:4:4:3:1 or 2:2:2:1:1, and inosine:cytidine:GMP:uridine:thymidine=4:4:4:3:1.

Most preferably, the present composition is used in the form of a parenteral solution for intravenous administration. The composition is usable also in the form of a powder, solution, suspension, emulsion, granules or the like for enteral administration such as through the mouth or gastrointestinal tracts. The dosage form of the composition can be suitably selected according to the purpose, etc.

The present composition can be prepared in the form of a parenteral solution which is the most preferable form, by substantially the same method as usual parenteral solutions of amino acids, electrolytes, etc. Typically, for example, such a parenteral solution can be prepared by dissolving the desired nucleic acid compounds in distilled water or the like for injection, adding additives to the solution when so desired and sterilizing the resulting aqueous solution by heating or filtration. Examples of suitable additives are stabilizers such as sodium sulfite, sodium bisulfite, sodium pyrosulfite and sodium thiosulfate, pH adjusting agents such as hydrochloric acid, acetic acid, lactic acid, malic acid, citric acid and sodium hydroxide, etc.

To prevent the amino acids in the living body from being consumed as an energy source without being converted to proteins, carbohydrates such as glucose, fructose, xylitol, sorbitol and maltose can be incorporated into the present composition. Furthermore, improved effects can be achieved by adding to the composition other ingredients, such as lipids, vitamins, electrolytes and trace elements, which are generally known for use in patenteral solutions of this type. Examples of useful lipids are soybean oil, cotton seed oil, sesame oil, yolk lecithin, soybean lecithin, etc. Examples of suitable vitamins are vitamin A, vitamin B, vitamin $B_2$, vitamin $B_6$, nicotinic acid, pantothenic acid, vitamin C, vitamin D, vitamin E, biotin, folic acids, etc. Examples of useful electrolytes are sodium chloride, sodium acetate, potassium chloride, magnesium sulfate, magnesium chloride, calcium chloride, dipotassium phosphate, sodium biphosphate, etc. Examples of useful trace elements are iron, zinc, manganese, copper, iodine, cobalt, etc.

The present composition can be in the form of a powdery preparation which is made into a solution when to be used. Such a powdery preparation can be produced easily by a suitable known method, such as freeze-drying, with or without addition of additives.

The parenteral solution of nucleic acid components thus prepared according to the invention has a pH range as broad as the conventional parenteral solutions, from usually of 3.0 to 9.0, preferably 3.0 to 8.0, more preferably 5.0 to 8.0. The parenteral solution thereof has a nucleic acid component concentration of 0.5 to 10 W/V %, preferably 2 to 8 W/V %.

The present parenteral solution of nucleic acid components is prepared in the form of a sterilized aqueous solution and is given intravenously via a peripheral or central vein, or enterally, whereby an outstanding nutritional replenishment effect can be achieved as contemplated.

When the present composition is given enterally, the parenteral solution may be used as it is, while the composition can be used also in the form of a powder, liquid, suspension, emulsion, granules or the like. In this case, the effective components are formulated into a preparation of the desired form along with usual additives.

Examples of useful additives are those suited to the form of preparation and usually used for pharmaceuticals, such as diluent, filler, extender, binder, suspending agent, disintegrator, surfactant, lubricant, excipient, etc.

The preparation may further incorporate therein usual solubilizing agent, buffer, analgesic, preservative, coloring agent, perfume, flavoring, sweetener, etc. when required. These additives are selected in accordance with the unit form of the composition to be administered, whereby a satisfactory nutritional replenishing effect can be obtained as is the case with the parenteral solution. When preparing an isotonic solution for formulating liquid, suspension or emulsion preparations, a sufficient amount of common salt, glucose or glycerin may be incorporated into the preparation.

The composition of the present invention is parenterally given to patients with impaired protein metabolism for whom it is difficult or impossible to orally take a diet or nutrients, for example, owing to liver diseases, gastrointestinal diseases, cancer, burn, surgery or some other cause. When given, the composition provides nutrients, further accelerates in vivo protein metabolism and enhances effective use of amino acids to assure satisfactory nutrition control and nitrogen balance. These effects become more pronounced when the composition is given conjointly with an amino acid preparation, resulting in promoted in vivo synthesis of proteins from the amino acids administered and permitting use of the amino acids with greaty improved efficiency. Accordingly when the present composition is administered to patients in combination with an amino acid preparation which fails to produce a sufficient effect if used singly, it becomes possible to assure more satisfactory nutrition control and nitrogen balance.

In the case where a known amino acid parenteral solution and the parenteral solution of nucleic acid components of the invention are to be given in combination, the two solutions may be mixed together into a single solution for administration, or the solutions may be given as two solutions. In either case, the nucleic acid compounds are given in such amount that the weight ratio of nucleic acid compounds to amino acids is usually 1:20 to 1:1, preferably 1:12 to 1:3. For use as a single solution, the two solutions are mixed into a parenteral solution containing the amino acids and the nucleic acid compounds in the above ratio. When the two solutions are given separately, they are used in such amounts that the two kinds of effective components will be in the above ratio.

Even when the present composition is used in a form other than the parenteral solution, the composition, if used in combination with an amino acid preparation, produces the same effect as is the case with the parenteral solution. Needless to say, the present composition is usable in combination with nutrient preparations other than amino acid preparations, such as protein preparations, glucose, etc.

The dosage of the present composition is widely varied in accordance with the pathological condition, nutritional condition, age and body weight of the patient, the kind of preparation to be used conjointly, etc. The composition is given generally at a daily dose of 1 to 50 grams, preferably 6 to 16 grams, of the effective components per adult. When in the form of a parenteral solution, the composition is given usually at a daily dose of 20 to 500 ml, preferably 30 to 200 ml, per adult.

Depending on the pathological condition of the patient, the present composition is usable also as an auxiliary therapeutic agent in combination with curing agents for injuries, ulcers and cancers, antibiotic substances, etc. This serves to cure diseases much earlier than when such curing agents are used singly and also to reduce the dose of pharmaceuticals, hence desirable.

Typical preparation examples of parenteral compositions of nucleic acid components according to the invention are given below. In these examples, the mole ratios are approximate values.

PREPARATION EXAMPLE 1

| Nucleic acid component | W/V % | mmol/l | Mole ratio |
|---|---|---|---|
| 5'-AMP.2Na | 2.34 | 59.8 | 4 |
| 5'-CMP.2Na | 2.20 | 59.9 | 4 |
| 5'-GMP.2Na | 2.44 | 59.9 | 4 |
| 5'-UMP.2Na | 1.65 | 44.8 | 3 |
| Thymidine | 0.36 | 14.9 | 1 |
| Total content of free nucleic acid components | 8.0 W/V % | | |

Pure crystals of nucleic acid components were added to sufficient distilled water for injection in amounts to form the above composition and dissolved by stirring. A 0.3 g quantity of sodium bisulfite was added to the solution as a stabilizer, and the solution was adjusted to a pH of about 7.4 with hydrochloric acid serving as a pH adjusting agent. The aqueous solution of nucleic acid components obtained was sterilized by filtration and poured into a container. The container was closed after replacing the interior air by nitrogen. The solution was then sterilized in an autoclave at 105° C. for 40 minutes to obtain a parenteral solution of nucleic acid components of the invention (total concentration of free nucleic acid components 8.0 W/V %).

PREPARATION EXAMPLE 2

| Nucleic acid component | W/V % | mmol/l | Mole ratio |
|---|---|---|---|
| 5'-CMP.2Na | 2.21 | 60.2 | 4 |
| 5'-GMP.2Na | 2.45 | 60.2 | 4 |
| 5'-UMP.2Na | 1.66 | 45.1 | 3 |
| 5'-IMP.2Na | 2.36 | 60.2 | 4 |
| Thymidine | 0.36 | 14.9 | 1 |
| Total content of free nucleic acid components | 8.0 W/V % | | |

Pure crystals of nucleic acid components were added to distilled water for injection in amounts sufficient to form the above composition and dissolved by stirring. A 0.3 g quantity of sodium bisulfite was added to the solution as a stabilizer, and the solution was adjusted to a pH of about 7.3 with acetic acid serving as a pH adjusting agent. The aqueous solution of nucleic acid components obtained was sterilized by filtration and filled into a container. The container was closed after replacing the interior air by nitrogen. The solution was then sterilized in an autoclave at 115° C. for 40 minutes to obtain a parenteral solution of nucleic acid components of the invention (total concentration of free nucleic acid components 8.0 W/V %).

PREPARATION EXAMPLE 3

| Nucleic acid component | W/V % | mmol/l | Mole ratio |
|---|---|---|---|
| 5'-CMP.2Na | 1.12 | 30.5 | 2 |
| 5'-GMP.2Na | 1.24 | 30.5 | 2 |
| 5'-UMP.2Na | 0.56 | 15.2 | 1 |
| 5'-IMP.2Na | 1.50 | 30.6 | 2 |
| Thymidine | 0.37 | 15.3 | 1 |
| Total content of free nucleic acid components | 4.0 W/V % | | |

Pure crystals of nucleic acid components were added to distilled water for injection in amounts sufficient to form the above composition and dissolved by stirring. A 0.3 quantity of sodium bisulfite was added to the solution as a stabilizer, and the solution was adjusted to a pH of about 6.4 with hydrochloric acid serving as a pH adjusting agent. The aqueous solution of nucleic acid components obtained was sterilized by filtration and filled into a container. The container was closed after replacing the interior air by nitrogen. The solution was then sterilized in an autoclave at 105° C. for 40 minutes to obtain a parenteral solution of nucleic acid components of the invention (total concentration of free nucleic acid components 4.0 W/V %).

PREPARATION EXAMPLE 4

| Nucleic acid component | W/V % | mmol/l | Mole ratio |
|---|---|---|---|
| Inosine | 0.80 | 29.8 | 4 |
| Cytidine | 0.73 | 30.0 | 4 |
| 5'-GMP.2Na | 1.22 | 30.0 | 4 |
| Uridine | 0.55 | 22.5 | 3 |
| Thymidine | 0.18 | 7.4 | 1 |
| Total content of free nucleic acid components | 3.4 W/V % | | |

Pure crystals of nucleic acid components were added to distilled water for injection in amounts sufficient to form the above composition and dissolved by stirring. A 0.3 g quantity of sodium bisulfite was added to the solution as a stabilizer, and the solution was adjusted to a pH of about 8.0 with sodium hydroxide serving as a pH adjusting agent. The aqueous solution of nucleic acid components obtained was sterilized by filtration and filled into a container. The container was closed after replacing the interior air by nitrogen. The solution was then sterilized in an autoclave at 105° C. for 40 minutes to obtain a parenteral solution of nucleic acid components of the invention (total concentration of free nucleic acid components 3.4 W/V %).

PREPARATION EXAMPLE 5

In the same manner as in Preparation Example 1, a parenteral solution of the following composition was prepared according to the invention (total concentration of free nucleic acid components 2.0 W/V %).

| Nucleic acid component | W/V % | mmol/l | Mole ratio |
|---|---|---|---|
| Inosine | 0.87 | 32.4 | 1 |
| 5'-AMP.2Na | 1.27 | 32.5 | 1 |
| Total content of free nucleic acid | 2.0 W/V % | | |

PREPARATION EXAMPLE 6

In the same manner as in Preparation Example 1, a parenteral solution of the following composition was prepared according to the invention (total concentration of free nucleic acid components 4.0 W/V %).

| Nucleic acid component | W/V % | mmol/l | Mole ratio |
|---|---|---|---|
| 5'-CMP.2Na | 2.27 | 61.8 | 1 |
| 5'-UMP.2Na | 2.27 | 61.7 | 1 |
| Total content of free nucleic acid components | | 4.0 W/V % | |

PREPARATION EXAMPLE 7

In the same manner as in Preparation Example 1, a parenteral solution of the following composition was prepared according to the invention (total concentration of free nucleic acid components 5.0 W/V %).

| Nucleic acid component | W/V % | mmol/l | Mole ratio |
|---|---|---|---|
| 5'-AMP.2Na | 2.93 | 74.9 | 1 |
| 5'-CMP.2Na | 2.73 | 74.4 | 1 |
| Total content of free nucleic acid components | | 5.0 W/V % | |

PREPARATION EXAMPLE 8

In the same manner as in Preparation Example 1, a parenteral solution of the following composition was prepared according to the invention (total concentration of free nucleic acid components 2.0 W/V %).

| Nucleic acid component | W/V % | mmol/l | Mole ratio |
|---|---|---|---|
| Uracil | 0.11 | 9.8 | 1 |
| 5'-CMP | 0.95 | 29.4 | 3 |
| 5'-TMP | 0.94 | 29.2 | 3 |
| Total content of free nucleic acid components | | 2.0 W/V % | |

PREPARATION EXAMPLE 9

In the same manner as in Preparation Example 1, a parenteral solution of the following composition was prepared according to the invention (total concentration of free nucleic acid components 4.0 W/V %).

| Nucleic acid component | W/V % | mmol/l | Mole ratio |
|---|---|---|---|
| Cytosine | 0.75 | 67.5 | 2 |
| Uridine | 0.82 | 33.6 | 1 |
| 5'-GMP.2Na | 2.72 | 66.8 | 2 |
| Total content of free nucleic acid components | | 4.0 W/V % | |

PREPARATION EXAMPLE 10

In the same manner as in Preparation Example 1, a parenteral solution of the following composition was prepared according to the invention (total concentration of free nucleic acid components 8.0 W/V %).

| Nucleic acid component | W/V % | mmol/l | Mole ratio |
|---|---|---|---|
| 5'-AMP.2Na | 3.04 | 77.7 | 1 |
| 5'-CMP.2Na | 2.84 | 77.4 | 1 |
| 5'-GMP.2Na | 3.14 | 77.1 | 1 |
| Total content of free nucleic acid components | | 8.0 W/V % | |

PREPARATION EXAMPLE 11

In the same manner as in Preparation Example 1, a parenteral solution of the following composition was prepared according to the invention (total concentration of free nucleic acid components 4.0 W/V %).

| Nucleic acid component | W/V % | mmol/l | Mole ratio |
|---|---|---|---|
| Cytosine | 0.08 | 7.2 | 1 |
| Thymidine | 0.36 | 14.9 | 2 |
| 5'-UMP.2Na | 1.66 | 45.1 | 6 |
| 5'-IMP.2Na | 2.37 | 60.4 | 8 |
| Total content of free nucleic acid components | | 4.0 W/V % | |

PREPARATION EXAMPLE 12

In the same manner as in Preparation Example 1, a parenteral solution of the following composition was prepared according to the invention (total concentration of free nucleic acid components 6.0 W/V %).

| Nucleic acid component | W/V % | mmol/l | Mole ratio |
|---|---|---|---|
| Uridine | 0.73 | 29.9 | 1 |
| 5'-GMP.2Na | 2.47 | 60.7 | 2 |
| 5'-UMP | 0.97 | 29.9 | 1 |
| 5'-IMP.2Na | 2.37 | 60.4 | 2 |
| Total content of free nucleic acid components | | 6.0 W/V % | |

PREPARATION EXAMPLE 13

In the same manner as in Preparation Example 1, a parenteral solution of the following composition was prepared according to the invention (total concentration of free nucleic acid components 8.0 W/V %).

| Nucleic acid component | W/V % | mmol/l | Mole ratio |
|---|---|---|---|
| 5'-CMP.2Na | 2.22 | 60.5 | 4 |
| 5'-UMP.2Na | 1.67 | 45.4 | 3 |
| 5'-IMP.2Na | 4.74 | 120.9 | 8 |

-continued

| Nucleic acid component | W/V % | mmol/l | Mole ratio |
|---|---|---|---|
| Thymidine | 0.37 | 15.3 | 1 |
| Total content of free nucleic acid components | | 8.0 W/V % | |

PREPARATION EXAMPLE 14

In the same manner as in Preparation Example 1, a parenteral solution of the following composition was prepared according to the invention (total concentration of free nucleic acid components 8.0 W/V %).

| Nucleic acid component | W/V % | mmol/l | Mole ratio |
|---|---|---|---|
| 5'-CMP.2Na | 2.65 | 72.2 | 7.5 |
| 5'-UMP.2Na | 1.42 | 38.6 | 4 |
| 5'-IMP.2Na | 4.72 | 120.4 | 12.5 |
| Thymidine | 0.23 | 9.5 | 1 |
| Total content of free nucleic acid components | | 8.0 W/V % | |

PREPARATION EXAMPLE 15

In the same manner as in Preparation Example 1, a parenteral solution of the following composition was prepared according to the invention (total concentration of free nucleic acid components 8.0 W/V %).

| Nucleic acid component | W/V % | mmol/l | Mole ratio |
|---|---|---|---|
| 5'-CMP.2Na | 2.16 | 58.8 | 1 |
| 5'-GMP.2Na | 2.40 | 58.9 | 1 |
| 5'-UMP.2Na | 2.17 | 58.9 | 1 |
| 5'-IMP.2Na | 2.31 | 58.9 | 1 |
| Total content of free nucleic acid components | | 8.0 W/V % | |

PREPARATION EXAMPLE 16

In the same manner as in Preparation Example 1, a parenteral solution of the following composition was prepared according to the invention (total concentration of free nucleic acid components 6.0 W/V %).

| Nucleic acid component | W/V % | mmol/l | Mole ratio |
|---|---|---|---|
| Cytosine | 0.34 | 30.6 | 2 |
| Thymidine | 0.37 | 15.3 | 1 |
| 5'-GMP.2Na | 2.47 | 60.7 | 4 |
| 5'-UMP.2Na | 1.11 | 30.2 | 2 |
| 5'-IMP.2Na | 2.38 | 60.7 | 4 |
| Total content of free nucleic acid components | | 6.0 W/V % | |

PREPARATION EXAMPLE 17

In the same manner as in Preparation Example 1, a parenteral solution of the following composition was prepared according to the invention (total concentration of free nucleic acid components 4.0 W/V %).

| Nucleic acid component | W/V % | mmol/l | Mole ratio |
|---|---|---|---|
| 5'-dAMP | 0.59 | 17.8 | 1 |
| 5'-ATP | 0.90 | 17.7 | 1 |
| 5'-GMP | 0.64 | 17.6 | 1 |
| 5'-UDP | 0.71 | 17.6 | 1 |
| 5'-IMP | 0.62 | 17.8 | 1 |
| 5'-dCMP | 0.54 | 17.6 | 1 |
| Total content of free nucleic acid components | | 4.0 W/V % | |

PREPARATION EXAMPLE 18

In the same manner as in Preparation Example 1, a parenteral solution of the following composition was prepared according to the invention (total concentration of free nucleic acid components 8.0 W/V %).

| Nucleic acid component | W/V % | mmol/l | Mole ratio |
|---|---|---|---|
| Cytosine | 0.33 | 29.7 | 2 |
| Inosine | 0.40 | 14.9 | 1 |
| 5'-AMP.2Na | 1.17 | 29.9 | 2 |
| 5'-UMP.2Na | 2.21 | 60.0 | 4 |
| 5'-GMP.2Na | 2.46 | 60.4 | 4 |
| 5'-IMP.2Na | 2.35 | 59.9 | 4 |
| Total content of free nucleic acid components | | 8.0 W/V % | |

PREPARATION EXAMPLE 19

In the same manner as in Preparation Example 1, a parenteral solution of the following composition was prepared according to the invention (total concentration of free nucleic acid components 10.0 W/V %).

| Nucleic acid component | W/V % | mmol/l | Mole ratio |
|---|---|---|---|
| Thymidine | 0.36 | 14.9 | 1 |
| 5'-CMP.2Na | 2.21 | 60.2 | 4 |
| 5'-GMP.2Na | 2.46 | 60.4 | 4 |
| 5'-UMP.2Na | 2.22 | 60.3 | 4 |
| 5'-IMP.2Na | 2.36 | 60.2 | 4 |
| 5'-TMP.2Na | 1.65 | 45.1 | 3 |
| Total content of free nucleic acid components | | 10.0 W/V % | |

PREPARATION EXAMPLE 20

In the same manner as in Preparation Example 4, a parenteral solution of the following composition was prepared according to the invention.

| Nucleic acid component | W/V % | mmol/l | Mole ratio |
|---|---|---|---|
| Inosine | 0.81 | 30.2 | 1 |
| 5'-GMP.2Na | 2.46 | 60.4 | 2 |
| Total content of free nucleic acid components | | 3.0 W/V % | |

PREPARATION EXAMPLE 21

In the same manner as in Preparation Example 1, a parenteral solution of the following composition was prepared according to the invention.

| Nucleic acid component | W/V % | mmol/l | Mole ratio |
|---|---|---|---|
| Inosine | 0.41 | 15.3 | 1 |
| 5'-AMP.2Na | 1.79 | 45.8 | 3 |
| 5'-UMP.2Na | 1.14 | 31.0 | 2 |
| Total content of free nucleic acid components | | 3.0 W/V % | |

PREPARATION EXAMPLE 22

In the same manner as in Preparation Example 1, a parenteral solution of the following composition was prepared according to the invention.

| Nucleic acid component | W/V % | mmol/l | Mole ratio |
|---|---|---|---|
| Inosine | 0.80 | 29.8 | 2 |
| 5'-CMP.2Na | 2.18 | 59.3 | 4 |
| 5'-UMP.2Na | 2.18 | 59.2 | 4 |
| Thymidine | 0.36 | 14.9 | 1 |
| Total content of free nucleic acid components | | 5.0 W/V % | |

PREPARATION EXAMPLE 23

In the same manner as in Preparation Example 4, a parenteral solution of the following composition was prepared according to the invention.

| Nucleic acid component | W/V % | mmol/l | Mole ratio |
|---|---|---|---|
| Uridine | 0.37 | 15.2 | 1 |
| 5'-CMP.2Na | 2.23 | 60.7 | 4 |
| 5'-GMP.2Na | 2.47 | 60.7 | 4 |
| 5'-IMP.2Na | 2.38 | 60.7 | 4 |
| Thymidine | 0.36 | 14.9 | 1 |
| Total content of free nucleic acid components | | 7.0 W/V % | |

PREPARATION EXAMPLE 24

In the same manner as in Preparation Example 4, a parenteral solution of the following composition was prepared according to the invention.

| Nucleic acid component | W/V % | mmol/l | Mole ratio |
|---|---|---|---|
| Inosine | 0.80 | 29.8 | 2 |
| 5'-CMP.2Na | 2.75 | 74.9 | 5 |
| 5'-GMP.2Na | 2.44 | 59.9 | 4 |
| 5'-UMP.2Na | 2.76 | 75.0 | 5 |
| Thymidine | 0.36 | 14.9 | 1 |
| Total content of free nucleic acid components | | 8.2 W/V % | |

PREPARATION EXAMPLE 25

In the same manner as in Preparation Example 4, a parenteral solution of the following composition was prepared according to the invention.

| Nucleic acid component | W/V % | mmol/l | Mole ratio |
|---|---|---|---|
| Inosine | 0.80 | 29.8 | 2 |
| Cytidine | 0.36 | 14.8 | 1 |
| 5'-CMP.2Na | 1.10 | 30.0 | 2 |
| 5'-GMP.2Na | 0.61 | 15.0 | 1 |
| 5'-UMP.2Na | 1.10 | 29.9 | 2 |
| Thymidine | 0.36 | 14.9 | 1 |
| Total content of free nucleic acid components | | 4.0 W/V % | |

PREPARATION EXAMPLE 26

In the same manner as in Preparation Example 4, a parenteral solution of the following composition was prepared according to the invention.

| Nucleic acid component | W/V % | mmol/l | Mole ratio |
|---|---|---|---|
| Inosine | 0.80 | 29.8 | 4 |
| Uridine | 0.55 | 22.5 | 3 |
| 5'-AMP.2Na | 1.17 | 29.9 | 4 |
| 5'-CMP.2Na | 2.18 | 59.4 | 8 |
| 5'-GMP.2Na | 1.19 | 29.2 | 4 |
| 5'-UMP.2Na | 1.65 | 44.8 | 6 |
| Thymidine | 0.18 | 7.4 | 1 |
| Total content of free nucleic acid components | | 7.0 W/V % | |

PREPARATION EXAMPLE 27

In the same manner as in Preparation Example 4, a parenteral solution of the following composition was prepared according to the invention.

| Nucleic acid component | W/V % | mmol/l | Mole ratio |
|---|---|---|---|
| Inosine | 0.81 | 30.2 | 2 |
| Cytidine | 0.73 | 30.0 | 2 |
| Uridine | 0.37 | 15.2 | 1 |
| 5'-CMP.2Na | 1.11 | 30.2 | 2 |
| 5'-GMP.2Na | 2.46 | 60.4 | 4 |
| 5'-IMP.2Na | 1.77 | 45.1 | 3 |
| 5'-UMP.2Na | 1.11 | 30.2 | 2 |
| Thymidine | 0.37 | 15.3 | 1 |
| Total content of free nucleic acid components | | 8.0 W/V % | |

Typical examples are given below wherein compositions for enteral administration were prepared according to the invention.

PREPARATION EXAMPLE 28

| | |
|---|---|
| 5'-AMP.2Na | 2.93 g |
| 5'-CMP.2Na | 2.73 g |

Pure crystals of the above nucleic acid components were passed through a 60-mesh screen, and the above-mentioned amounts of the minus fractions were uniformly mixed together and placed into a glass container to obtain a powdery composition according to the invention. The composition contained the components, i.e. 5'-AMP.2Na and 5'-CMP.2Na, in a mole ratio of about 1:1.

When dissolved in a suitable amount of purified water, the powdery composition can be made into a preparation of suitable concentration for enteral administration.

PREPARATION EXAMPLE 29

| 5'-CMP.2Na | 2.27 W/V % |
| 5'-UMP.2Na | 2.27 W/V % |
| Purified white sugar | 20.00 W/V % |
| Sodium bisulfite | 0.03 W/V % |
| Ethyl p-oxybenzoate | 0.009 W/V % |
| Butyl p-oxybenzoate | 0.006 W/V % |

Purified water was heated, and purified white sugar serving as a sweetener was dissolved in the water with stirring. To obtain the above composition, to the solution thereafter cooled were added nucleic acid components, sodium bisulfite serving as a stabilizer, and ethyl p-oxybenzoate and butyl p-oxybenzoate dissolved in a small amount of ethanol and serving as preservatives, followed by stirring. The volume of the resulting solution was adjusted with the addition of purified water, and the solution was filtered and then placed into a glass container. The container was sealed off after replacing the interior air by nitrogen. The solution was thereafter sterilized by heating to obtain a liquid composition according to the invention.

The composition contained the nucleic acids, i.e. 5'-CMP.2Na and 5'-UMP.2Na, in a mole ratio of about 1:1. The total content of free nucleic acid components was 4.0 W/V %.

PREPARATION EXAMPLE 30

| 5'-AMP.2Na | 2.34 g |
| 5'-CMP.2Na | 2.20 g |
| 5'-GMP.2Na | 2.44 g |
| 5'-UMP.2Na | 1.65 g |
| Thymidine | 0.36 g |
| Starch | 91.01 g |

Pure crystals of nucleic acid components in such amounts as to give the above composition were passed through a 60-mesh screen, and the ingredients were uniformly mixed together along with starch serving as an excipient to obtain a dispersion of nucleic acid components according to the invention.

The composition contained the nucleic acid components, i.e. 5'-AMP.2Na, 5'-CMP.2Na, 5'-GMP.2Na, 5'-UMP.2Na and thymidne, in a mole ratio of about 4:4:4:3:1. The total content of free nucleic acid components was 8.0 W/W %.

PREPARATION EXAMPLE 31

| Uridine | 0.73 g |
| 5'-GMP.2Na | 2.47 g |
| 5'-UMP | 0.97 g |
| 5'-IMP.2Na | 2.37 g |
| Starch | 91.46 g |
| Methylcellulose | 2.00 g |

Pure crystals of nucleic acid components in such amounts as to give the above composition were passed through a 100-mesh screen, and the ingredients were then uniformly mixed together with addition of starch serving as an excipient and also as a disintegrator. The mixture was further kneaded with an aqueous solution of methylcellulose serving as a binder, then passed through a 24-mesh screen, thereafter dried and further passed through a 20-mesh screen to obtain a fraction of uniform particle size, whereby a granular preparation of nucleic acid components was obtained according to the invention.

The composition contained the nucleic acid components, i.e. uridine, 5'-GMP.2Na, 5'-UMP and 5'-IMP.2Na, in a mole ratio of approximately 1:2:1:2. The total content of free nucleic acid components was 6 W/W %.

The parenteral solutions of the invention prepared in some of the foregoing preparation examples were tested by animal experiments with the results described below in detail.

TEST EXAMPLE 1

Male Wistar rats weighing about 250 g were anesthetized with pentobarbital. With a cannula inserted into jugular vein of each rat, 70% portion of the liver mass was removed from the rat according to the method of Higgins-Anderson (Arch. Pathol., 12, 186 (1931)). The rat was placed into a cage and given a hyperalimentation solution for three days immediately after the operation.

A hyperalimentation solution prepared by adding glucose, electrolyte and vitamins to a commercial amino acid parenteral solution (12%, FAO/WHO formulation) was given to a control group (hereinafter referred to as "group A"). The solution obtained in Preparation Example 2 according to the invention was added to the above solution, and the resulting solution was given to another group (hereinafter referred to as "group B"). The rats of each group were checked for nitrogen balance. With reference to experimental results obtained with normal rats, the solution of Preparation Example 2 was given in such an amount that it would not greatly influence the blood plasma component and the amount of uric acid excretion. Thus, the amount was such that the nucleic acid components were 1/10 of the amino acids given in weight ratio.

In each group, the amino acid dose was 8 g/kg/day, the total amount of water was 200 ml/kg/day and the total calory given was 200 Kcal/kg/day. On the day of the operation, 75% of these amounts were given.

The results are given in Table 1, which shows that the group B was superior to the group A in nitrogen balance.

TABLE 1

| Cumulative nitrogen balance for 3 days after operation (mg/kg) | |
| --- | --- |
| Group A (n = 10) | Group B (n = 10) |
| −210 ± 273 | +352 ± 183* |
| mean ± SE | |

*($p < 0.05$)

TEST EXAMPLES 2–7

Animal tests were conducted in the same manner as in Test Example 1, using the parenteral solutions of the invention obtained in Preparation Examples 3, 4, 5, 10, 14 and 15.

TABLE 2

Cumulative nitrogen balance for 3 days after operation (mg/kg)

| | Group A (n = 6) | Group B (n = 6) |
|---|---|---|
| Test Example 2 | −132 ± 189 | +318 ± 160 (Prep. Ex. 3) |
| Test Example 3 | −131 ± 137 | +389 ± 198 (Prep. Ex. 4) |
| Test Example 4 | −115 ± 129 | +147 ± 92 (Prep. Ex. 5) |
| Test Example 5 | 18 ± 109 | +251 ± 128 (Prep. Ex. 10) |
| Test Example 6 | −54 ± 117 | +287 ± 126 (Prep. Ex. 14) |
| Test Example 7 | −66 ± 144 | +304 ± 131 (Prep. Ex. 15) |
| | mean ± SE | |

Table 2 reveals that in each of Test Examples, the group B was superior to the group A.

The composition of the invention obtained in Preparation Example 28 for enteral administration was enterally given to test animals, with the results described below.

TEST EXAMPLE 8

Male Wistar rats weighing about 200 g were anesthetized with pentobarbital, and 70% portion of the liver mass was removed from each rat in the same manner as in Test Example 1. At the same time, the stomach was taken out, and a cannula was fixed to the forestomach for gastrostomy. The cannula was positioned subcutaneously with use of a silicone resin tube and connected to a pump tube. The solution to be tested was thereafter given continuously for 3 days. A commercial nutrient composition (comprising crystalline amino acids as protein source, dextrin as carbohydrates, soybean oil as fat, minerals and vitamins) was made into 33.4% solution (amount of nitrogen 8.09 mgN/g, calorific value of 116 Kcal/g), which was given to a control group (hereinafter referred to as "group A"). The composition of Preparation Example 28 was added to the above solution and given to another group of rats (hereinafter referred to as "group B"). The calorie value given to the group A was 100 Kcal/kg/day on the day of operation, or 200 Kcal/kg/day on the second and third days after operation. The composition of the invention was given to the group B in such an amount that it constituted 1/10 of the amino acids given in weight ratio.

The results are listed in Table 3 below, which shows that the group B was superior to the group A in nitrogen balance.

TABLE 3

Cumulative nitrogen balance for 3 days after operation (mg/kg)

| Group A (n = 6) | Group B (n = 6) |
|---|---|
| −12 ± 158 | +226 ± 116 |
| mean ± SE | |

I claim:

1. A composition of nucleic acid components for nutritional replenishment to a patient having impaired protein metabolism, comprising as effective components a combination of nucleic acid components or their pharmaceutically acceptable salts, said combination being selected from the group consisting of combinations (i) and (ii);
   (i) inosine-n'-monophosphate (IMP), guanosine-n'-monophosphate (GMP), cytidine-n'-monophosphate (CMP), uridine-n'-monophosphate (UMP) and thymidine, and
   (ii) inosine, cytidine, guanosine-n'-monophosphate (GMP), uridine and thymidine,
wherein n' is 2', 3' or 5'.

2. A composition as defined in claim 1 wherein the combination of nucleic acid components has the following mole ratio: IMP/GMP/CMP/UMP/thymidine=4:4:4:3:1 or 2:2:2:1:1.

3. A composition as defined in claim 1 wherein the combination of nucleic acid components has the following mole ration: inosine/cytidine/GMP/uridine/thymidine=4:4:4:3:1.

4. A composition as defined in claim 1, further comprising additives and an aqueous medium which are pharmaceutically suitable, said nucleic acid components and said additives being dissolved in the aqueous medium to form an aqueous solution, said solution being sterilized and being in the form of a parenteral solution.

5. A composition as defined in claim 1 which is in the form of a powdery mixture for enteral administration.

6. A composition as defined in claim 4 which is used in combination with an amino acid parenteral solution.

7. A composition as defined in claim 1, further comprising an aqueous medium, a sweetener, a stabilizer and a preservative which are pharmaceutically suitable, said nucleic acid components and said sweetener, stabilizer and preservative being dissolved in the aqueous medium to form an aqueous solution, said solution being sterilized and being in the form of a liquid composition for enteral administration.

8. A method of nutritional replenishment which comprises administering to a patient with impaired protein metabolism an effective amount of a composition comprising as effective components a combination of nucleic acid components or their pharmaceutically acceptable salts, said combination being selected from the group consisting of combinations (i) and (ii);
   (i) inosine-n'-monophosphate (IMP), guanosine-n'-monophosphate (GMP), cytidine-n'-monophosphate (CMP), uridine-n'-monophosphate (UMP) and thymidine, and
   (ii) inosine, cytidine, guanosine-n'-monophosphate (GMP), uridine and thymidine,
wherein n' is 2', 3' or 5'.

9. A method of nutritional replenishment as defined in claim 8 wherein said composition further comprises additives and an aqueous medium which are pharmaceutically suitable, said nucleic acid components and said additives being dissolved in the aqueous medium to form an aqueous solution, said solution being sterilized and being in the form of a parenteral solution.

10. A method as defined in claim 9 wherein the composition is given in combination with an amino acid parenteral solution.

11. A method as defined in claim 8 wherein the composition is given at a daily dose of 1 to 50 g, calculated as the effective components, per adult.

* * * * *